United States Patent [19]

Hancock et al.

[11] Patent Number: 5,723,130

[45] Date of Patent: Mar. 3, 1998

[54] ADJUVANTS FOR VACCINES AGAINST RESPIRATORY SYNCYTIAL VIRUS

[76] Inventors: Gerald E. Hancock, 50 Plains Rd., Honeoye Falls, N.Y. 14472; Dan J. Speelman, 4215 Pine Haven La., Sanford, N.C. 27330; Patrick J. Frenchick, 6601 Rexford Dr., Lincoln, Nebr. 68506

[21] Appl. No.: 553,332

[22] PCT Filed: May 24, 1994

[86] PCT No.: PCT/US94/05833

§ 371 Date: Sep. 16, 1996

§ 102(e) Date: Sep. 16, 1996

[87] PCT Pub. No.: WO94/27636

PCT Pub. Date: Dec. 8, 1994

[51] Int. Cl.⁶ .......... A61K 39/155; A61K 39/12; A61K 39/00; C07K 5/00
[52] U.S. Cl. .......... 424/211.1; 424/184.1; 424/204.1; 530/350
[58] Field of Search .......... 424/211.1, 204.1, 424/184.1

[56] References Cited

U.S. PATENT DOCUMENTS 5,057,540 10/1991 Kensil et al. .......... 514/25
5,194,595 3/1993 Wathen .......... 530/395

OTHER PUBLICATIONS

Schneerson, et al, 1991, "Evaluation of Monophosphoryl Lipid A as an Adjuvant ... " J. Immunol. 147(7):2136–2140.
Stott, et al, 1986, "Human Respiratory Syncytial Virus ... " J. of Virology 60(2):607–613.
Wertz, et al, 1987, "Expression of the Fusion Protein of Human ... " J. Virol. 61(2):293–301.

*Primary Examiner*—Lynette F. Smith
*Attorney, Agent, or Firm*—Alan M. Gordon

[57] ABSTRACT

Vaccine formulations and therapeutic methods therefor containing respiratory syncytial viral proteins or immunological fragment and an adjuvant selected from the group consisting of QS-21 3-deacylated monophosphoryl lipid A, monophosphoryl lipid A and combination are described herein. Presence of the adjuvant(s) significantly increases the humoral and cell-mediated immunogenicity of the RSV proteins.

6 Claims, 2 Drawing Sheets

ADJUVANTS FOR VACCINES AGAINST RESPIRATORY SYNCYTIAL VIRUS

This application is a 371 of PCT/US94/05833 filed May 24, 1994.

BACKGROUND OF THE INVENTION

Respiratory Syncytial Virus (RSV) is a major cause of lower respiratory disease in infancy and early childhood (McIntosh and Chanock, 1985, in *Virology*, Fields, B. (ed), Raven, N.Y., pp. 1285–1304). In all geographical areas, it is the major cause of bronchiolitis and pneumonia in infants and young children. The agent reinfects frequently during childhood, but illness produced by reinfection is generally milder than that associated with the initial infection and rarely causes major problems.

RS virus is an enveloped RNA virus of the family ParamyxoViridae and of the genus pneumovirus. The two major envelope proteins are the G protein, which is responsible for attachment of the virus to the host cell membrane, and the fusion protein (F protein), which is responsible for fusing the virus and cell membranes. Virus-cell fusion is a necessary step for infection. Fusion protein is also required for cell-cell fusion which is another way to spread the infection from an infected cell to an uninfected cell.

Antibodies directed against the fusion protein or against the G protein can neutralize the virus. However, only antibodies to the fusion protein will block the spread of the virus between cells, i.e., have anti-fusion activity. Thus, antibodies to the fusion protein will protect against circulating virus as well as inhibit the spread, between cells, of an established infection. Antibodies to the fusion protein (both polyclonal antisera against purified fusion protein and monoclonal antibodies which contain both neutralizing and anti-fusion activity) have been found to be protective in animal models against infection (Walsh et al., 1984, Infect. Immun. 43: 756–758).

A practical means for protection of infants and young children against upper and lower respiratory disease would be protective vaccination against RS virus. Vaccination of expectant mothers (active immunization) would protect young children by passive transfer of immunity, either transplacentally, or through the mother's milk. Several approaches to an RS virus vaccine are possible, but some of them have proven unsuccessful in the past.

Vaccination with killed RS virus vaccine has been tried and found to be ineffective (Kim et al., 1969, Am. J. Epid. 89: 422). Not only were children not protected, but in some cases, subsequent infections with RS virus resulted in atypical and more severe disease than in the unimmunized controls. This phenomenon is not unique to RS virus and has been seen also in killed paramyxovirus vaccines such as measles. It has been suggested that the reason for the failure of the past inactivated RS virus vaccine was due to inactivation of the biologically functional epitopes on either or both of the viral envelope qlycoproteins. That is to say, the neutralizing and fusion epitopes on the killed virus vaccine were "denatured". As a result, the vaccinated subject did not experience the biologically functional neutralizing and fusion epitopes. Therefore, when the vaccinated subject encountered a live virus, the resultant antibody response did not yield protective immunity. Instead, there was an antibody mediated inflammatory response which often resulted in a more severe disease (Choppin and Scheid, 1980, Rev. Inf. Dis. 2: 40–61).

The second approach to an RS virus vaccine has been to attenuate live virus. Temperature sensitive mutants (Wright et al., 1982, Infect. Immun. 37: 397–400) and passage attenuated virus (Belshe et al., 1982, J. Inf. Dis. 145: 311–319) have proven to be poorly infectious and not efficacious in the prevention of disease when used as immunogens in RS virus vaccines. However, in these cases, there was no atypical disease as a result of vaccination.

Based on our current knowledge of the structure of RS virus and the immune response to infection, it is clear that a useful vaccine to this virus must be effective in inducing production of antibodies to the fusion protein and/or the G protein. Of particular importance to protective immunity is the production of antibodies that inhibit fusion and therefore, can stop the spread of virus between cells in the respiratory tract. Additionally, it is helpful to induce a cell mediated immune response, including the stimulation of cytotoxic T cells (CTL's) which are useful against RS virus infected cells. The various vaccine formulations of the present invention are directed to meeting both these objectives.

SUMMARY OF THE INVENTION

This invention pertains to the discovery of certain adjuvants that are capable of increasing the immunological response to envelope proteins of respiratory syncytial virus, specifically to RSV glycoprotein F and RSV glycoprotein G. In particular, it is shown herein that the adjuvant QS-21, or alternatively, 3D-monophosphoryl lipid A (MPL) plus alum, significantly increase the ability of antibodies raised against RSV glycoproteins F and/or G to neutralize the virus as well as provide immunological protection via cell-mediated response against the virus. Additionally, these adjuvants have been shown to prevent syncytia formation in vitally infected cells. Based on these findings, vaccine formulations can be made comprising envelope protein(s) of RSV and an adjuvant selected from QS-21, MPL, 3D-MPL and combinations. The formulation may optionally contain alum. The addition of alum can further boost the immunological response to the RSV antigen(s) when administered with these adjuvants. The presence of these adjuvants provides enhanced immunogenicity to the antigen by augmentation of the immune response, in particular, complement mediated plaque reduction neutralization when compared to alum. Additionally, the presence of adjuvant allows a vaccine to be made with a reduced amount of antigen(s).

DETAILED DESCRIPTION OF THE INVENTION

The present invention pertains to novel vaccine formulations and therapeutic uses therefore for prevention of RSV infection. The vaccine formulation of the present invention comprises an RSV protein or an immunological fragment thereof and an adjuvant that has been shown to boost the immunological response to the RSV protein. The adjuvant is selected from QS-21 and monophosphoryl lipid A and combinations thereof, and optionally alum. The presence of alum in the vaccine acts synergistically with MPL to elicit a neutralization response to RSV.

In one embodiment of the invention, QS-21 is formulated with RSV envelope protein G and/or F. QS-21 is a saponin which is purified from a crude *Ouillaja saponaria* extract and has been described by Kensil and Marciani, U.S. Pat.

No. 5,057,540. Antibodies raised against formulations comprising QS-21 and RSV protein F or RSV protein G and F can neutralize RS virus. The immunogenicity of RSV F and G proteins is greatly increased using QS-21 as the adjuvant compared to formulations that are not adjuvanted or that contain other known adjuvants, such as alum when used solely as the adjuvant.

Another aspect of the present invention is that the adjuvants can be employed in a vaccine with RSV G protein or F protein to elicit an immune response, such as antibody response, which neutralizes both subgroup A and subgroup B of the RSV virus. This is a significant discovery since other adjuvants, specifically alum, with G protein have been found to neutralize only the subgroup from which the protein0 is purified.

In another embodiment, MPL and specifically 3D-MPL can be used in combination with alum to produce a vaccine formulation that can enhance stimulation of complement dependent neutralizing antibodies to RSV. The immunogenicity of RSV subunit components is greatly increased with this adjuvant compared to formulations that are not adjuvanted or that contain alum as the sole adjuvant.

Proteins and polypeptides related to a neutralizing and/or fusion epitope(s) of the fusion protein and/or G protein of RS virus are useful as immunogens in a subunit vaccine to protect against lower respiratory disease and other disease symptoms of RS virus infection and can be formulated in the vaccines of the present invention. Subunit vaccines comprise the relevant immunogenic material necessary to immunize a host and the adjuvants, identified herein as potent immunomodulators. Vaccines prepared from genetically engineered immunogens, chemically synthesized immunogens and/or immunogens comprising authentic substantially pure RS virus fusion protein or fragments thereof alone or in combination with similarly prepared RS virus G protein or fragments thereof, which are capable of eliciting a protective immune response are particularly advantageous because there is no risk of infection of the recipients. Chimeric polypeptides comprising at least one immunogenic fragment from both RSV glycoproteins F and G can also be used in vaccine formulations of this invention. Such chimeric RSV polypeptides have been described by Wathen, U.S. Pat. No. 5,194,595, the teachings of which are incorporated herein by reference. The chimeric glycoprotein described below consists of the signal and extracellular domains of RSV F linked to the extracellular domain of RSV G.

The RS virus fusion protein and/or G protein and polypeptides can be purified from recombinants that express the neutralizing and/or fusion epitopes. Such recombinants include any bacterial transformants, yeast transformants, cultured insect cells infected with recombinant baculoviruses or cultured mammalian cells as known in the art, for example, such as Chinese hamster ovary cells that express the RS virus fusion protein epitopes. The recombinant protein or polypeptides can comprise multiple copies of the epitope of interest.

The RS virus fusion protein and/or G protein related protein or polypeptide can be chemically synthesized. Alternatively, the RS virus fusion protein related protein or polypeptide or G related protein can be isolated in substantially pure form from RS virus or cultures of cells infected with RS virus and formulated with the novel adjuvants as a vaccine against RSV.

Regardless of the method of production, the RS virus fusion protein or G protein, related protein or polypeptide is adjusted to an appropriate concentration and can be formulated with an adjuvant selected from QS-21 or MPL plus alum. MPL and its derivative 3-deacylated MPL (3D-MPL) can be co-formulated with TDM and squalene and used in vaccine formulations of the present invention. 3D-MPL may be obtained according to the methods described in British Patent No. 2220211 (Ribi Immunochem.).

The amount of protein in each vaccine dose is selected as an amount which induces an immunoprotective response without significant adverse side effects. Such amount will vary depending upon the immunogen used. Generally each dose will comprise from about 0.1 to about 100 μg of protein, with from about 5 to about 50 μg being preferred and from about 5 to about 25 μg/dose being alternatively preferred. The amount of adjuvant will be an amount that will induce an immunomodulating response without significant adverse side effect. An optional amount for a particular vaccine can be ascertained by standard studies involving observation of a vaccine's antibody titers and their virus neutralization capabilities. The amount of adjuvant will be from about 1 to about 100 μg/dose, with from about 5 to about 50 μg/dose being preferred, and from about 20 to about 50 μg/dose being alternatively preferred.

Immunopotency of vaccines containing the RS virus fusion or G protein or immunologic fragments thereof and genetic or physical mixtures thereof can be determined by monitoring the immune response of test animals following immunization with the purified protein, synthetic peptide or recombinant protein. Test animals may include but are not limited to mice, rats, rabbits, primates, and eventually human subjects. Methods of introduction of the immunogen may include intradermal, intramuscular, intraperitoneal, intravenous, subcutaneous, intranasal or any other standard routes of immunizations. The immune response of the test subjects can be analyzed by multiple approaches: (a) the reactivity of the resultant immune serum to authentic RS viral antigens, as assayed by known techniques, e.g., enzyme linked immunosorbant assay (ELISA), immunoblots, radio-immunoprecipitations, etc, (b) the ability of the immune serum to neutralize RS virus infectivity in vitro, (c) the ability of the immune serum to inhibit virus fusion in vitro, the ability of immunized animals to generate antigen dependent cytotoxic T lymphocyte (CTL) activity and (e) protection from RS virus infection.

Many methods may be used to administer the vaccine formulations described herein to humans for prophylatic purposes. These include, but are not limited to: intradermal, intramuscular, intraperitoneal, intravenous,subcutaneous and intranasal routes. The secretory IgA antibodies produced by the mucosal associated lymphoid tissue may play a major role in protection against RS virus infection by preventing the initial interaction of the pathogens with the mucosal surface, or by neutralizing the important epitopes of the pathogens that are involved in infection/or spreading of the disease. Stimulation of mucosal immune responses, including production of secretory IgA antibodies may be of major importance in conferring protection against lower and upper respiratory tract infection.

The polypeptides and proteins may generally be formulated at concentrations in the range of from about 0.1 μg to about 100 μg per dose. Physiologically acceptable media may be used as carriers. These include, but are not limited to: sterile water, saline, phosphate buffered saline and the like. Other suitable adjuvants may be added to the novel vaccine formulations of this invention and include, mineral gels, e.g., aluminum hydroxide, aluminum phosphate, etc. The immunogen may also be incorporated into liposomes or conjugated to polysaccharides and/or other polymers for use in a vaccine formulation.

The polypeptides and proteins that can be incorporated into vaccine formulations of the present invention may be linked to a soluble macromolecular carrier. Preferably, the carrier and the polypeptides and proteins are in excess of five thousand daltons after linking, and more preferably, the carrier is in excess of five kilodaltons. Preferably, the carrier is a polyamino acid, either natural or synthetic, which is immunogenic in animals, including humans. The manner of linking is conventional. Many linking techniques are disclosed in U.S. Pat. No. 4,629,783 which is incorporated herein by reference. Many cross-linking agents are disclosed in 1986–87 Handbook and General Catalog, Pierce Chemical Company, (Rockford, Ill.) pages 311–340.

Recombinant viruses are prepared that express RS virus fusion protein and/or G protein related epitopes. These viruses can be used to prepare inactivated recombinant viral vaccines to protect against lower respiratory infections and other disease symptoms of RS virus.

Inactivated vaccines are "dead" in the sense that their infectivity has been destroyed, usually by chemical treatment (e.g., formaldehyde). Ideally, the infectivity of the virus is destroyed without affecting the proteins which are related to immunogenicity of the virus. In order to prepare inactivated vaccines, large quantities of the recombinant virus expressing the RS virus fusion protein and/or G protein, related proteins or polypeptides must be grown in culture to provide the necessary quantity of relevant antigens. A mixture of inactivated viruses which express different epitopes may be used for the formulation of "multivalent" vaccines. In certain instances, these "multivalent" inactivated vaccines may be preferable to live vaccine formulation because of potential difficulties which mutual interference of live viruses administered together. In either case, the inactivated recombinant virus or mixture of viruses can be formulated with the adjuvant of this invention in order to enhance the immunological response to the antigens.

The vaccines of this invention can be administered to an individual to prevent an infection or disease symptoms associated with RSV. Such administration can be accomplished by a single dose or by multiple doses for eliciting a primary immune response in the individual. Typically multiple vaccination will be given three times at essentially two month intervals for humans. Booster doses may be given to stimulate an existingimmune response from previous vaccination or natural infection.

The following Examples are offered for the purpose of illustrating the present invention and are not to be construed to limit the scope of the present invention.

EXEMPLIFICATION

EXAMPLE 1

RSV Protein Preparation

A. Immunoaffinity fusion protein-1 (PFP-1)

PFP-1 is prepared by the procedure of Walsh et al. *J. Gen. Virol.* 66: 409–415 (1985) with the following modifications. The immunoaffinity eluted material is passed over a DEAE column and the flow through is collected, dialised against PBS/0.1% Triton X-100 and sterile filtered through a 0.2 μm filter.

B. Ion exchange fusion protein-2 (IF)

IF is prepared by passing clarified RSV-infected cell lkysate over a DEAE column. The flow through is collected and passed over a hydroxy-apatite (HA) column. Following HA elution, the eluted F protein is dialysed against PBS/0.1% Triton X-100, and sterile filtered through a 0.2 μm filter.

C. Immunoaffinity G protein (G)

G. protein is prepared by the procedure of Walsh et al. J. Gen. Virol. 66: 761–767 (1984) with the following modifications. Following elution, the G protein is passed over an immunoaffinity column specific for RSV F protein. The flow through is collected, dialysed against PSB/0.1% Triton X-100, and sterile filtered through a 0.2 μm filter.

D. F/G Protein Chimeric

F/G protein chimeric is prepared by U.S. Pat. No. 5,194,595 and provided by Upjohn Corporation.

EXAMPLE 2

Enzyme Immunoasay (EIA)

Antibody titer in serum samples is determined using an Enzyme Immunoassay (EIA) performed as follows:

RS virus fusion protein is diluted to 200 ng/ml in carbonate-bicarbonate buffer, pH 9.6. One hundred μl of the diluted antigen is added to each well of rows B-G of a flat-bottomed, 96 well NUNC™ assay plate. In rows A and H, 100 μl of carbonate-bicarbonate buffer alone is added to each well. The plate is covered and incubated for 2 hours at 37° C. with shaking and stored overnight at 4° C. to immobilize the antigen.

The supernatants are removed from the NUNC™ assay plate and the plate is washed with 0.1% Tween/PBS pH 7.4 and pat dried.

Three antibody samples are assayed on each plate. Each sample is first diluted to a primary dilution in 0.2% Tween, 0.01M EDTA/PBS pH 7.5 (0.2% TWN). The primary dilutions are further serially diluted as follows in a 96 well U-bottomed FALCON™ plate:

(a) The primary ilutions of the samples are inoculated into row 2 at 200 μl/well. Sample 1 is inoculated in triplicate, e.g., in wells A2, B2 and C2; Sample 2 in duplicate e.g., in wells D2, E2; Sample 3 in triplicate e.g., in wells F2, G2 an H2.

(b) 100 μl of 0.2% TWN were inoculated into each well of rows 3–12.

(c) Serial dilutions were created by transferring sequentially 100 μl from a well in row2 to the corresponding well in row 3 (e.g., B2 to B3; C2 to C3), a well in row 3 to the corresponding well in row 4, until row 12 was reached.

(d) To row 1, 100 μl of 0.2% TWN was added to each well as control.

One hundred μl of the primary dilutions are transferred from each well of the FALCON™ plate to the corresponding well in the NUNC™ plate, e.g., A2 (FALCON™) to A2 (NUNC™). The NUNC™ assay plate is covered and incubated for one hour at 37° C. with shaking The supernatants are removed from the assay plate, and the plate is washed with 0.1% Tween/PBS and pat dried.

Goat anti-Mouse IgG alkaline phosphatase conjugate (TAGO™) is diluted with 0.3% Tween/PBS pH 7.0 (0.3%TWN) to a working dilution, e.g., 1:1500. The diluted conjugate (100 μl) is added to each well in rows 2–12. The row 1, 100 μl of 0.3% TWN are added to each well as control. The plate is covered and incubated for 1 hour at 37°

C. with shaking. The inocula is then removed, and the plate is washed with 0.1% Tween/PBS pH 7.4 and pat dried.

To each and every well, 100 μl substrate solution, 1 mg/ml in diethanolamine buffer pH 9.8 (SIGMA-104™) are added. The enzymatic reaction is allowed to take place at room temperature for 1 hours. The reaction is stopped by adding 100 μl of 3N NaOH to each well. The extent of enzymatic reaction is determined by reading the optical density of 410 nm.

Rows A and H serve as negative controls because no antigen is present; row 1 also serves as a negative control because no antibodies are present.

EXAMPLE 3

Virus Neutralization Assay (Plaque Reduction Neutralization test, PRNT)

Test serum samples which are serially diluted and the positive control serum are heat inactivated at 56° C for 30 min. All sera are then diluted with an equal volume containing about 30 plaque forming units (PFU) of RS virus, and incubated at 37° C. for one hour, with (C' plus PRNT) or without (PET) the addition of 5% rabbit complement. A pool of human adult sera which had previously been characterized by enzyme immunoassay, neutralization and antifusion assays is used for positive control. Sera which had previously been characterized and was known to be non-immune is used as negative control.

Each incubated serum-virus mixture is inoculated to HEp-2 cells (ATCC No. CCL23) in separate wells of 96 well plates and virus absorption is allowed to take place for 2 hours at 37° C. The inocula are removed. The cell monolayers are washed and overlayed with modified Eagle's medium plus 5% fetal bovine serum and 1% SEPHADEX®, and incubated at 37° C. for 3 days. The overlay medium is removed and the cells are washed with phosphate buffered saline (PBS).

200 μl of chilled PBS-methanol (1:5) solution is added to each well, and the cells are fixed for 30 min. at room temperature. The PBS-methanol fixative is removed, an 200 μl per well of 5% CARNATION® instant milk in PBS, pH 6.8 (BLOTTO) is added. The plate is incubated for 30 minutes at 37° C.

The BLOTTO is removed. 50 μl per well of monoclonal antibodies against RS virus (previously titered and diluted with BLOTTO to a working concentration) is added, and the plate is incubated at 37° C. for 1 hour. The antibodies ae removed, and the fixed cells are washed twice with BLOTTO, 30 minutes each time.

50 μl/well of horseradish peroxidase conjugated goat anti-mouse IgG (diluted 1:250 in BLOTTO) is added and the plate is incubated for 1 hour at 37 μC. The goat antibodies are removed, and the fixed cells are again washed twice with BLOTTO, 30 minutes each time.

50 μl/well of a peroxidase substrate solution (0.05% 4-chloro-1-naphthol, 0.09% $H_2O_2$ in PBS pH 6.8) is added, and color is allowed to develop for 15–30 minutes at room temperature. The substrate solution is removed, and the wells are washed with water and air dried. The number of plaques in each well is determined.

The neutralization ability of a test serum sample is expressed as the dilution which results in a 60% reduction in plaque formation when compared to non-immune control serum. The results are tabulated in Tables 1–4.

Data in Tables 1, 2, 3 and 4 representing the EIA and Plaque Reduction Neutralization Test results show the improvement in the biological immune response with the use of these novel adjuvants when compared to alum alone. The vaccine formulations of RS virus fusion protein, G protein, mixtures thereof and F/G Chimeric protein with the novel adjuvants (with or without additional alum) were ignificantly enhanced when compared to formulations containing alum alone.

Immunogenicity of RSV F and G Proteins with Various Adjuvants[1]

Serological Titers by Assay[2] and Time

| Immunogen[3] | Adjuvant[4] | EIA-F (x1000) | | EIA-Ga (x1000) | | PRNT (A2) | | C'-PRNT (A2) | | PRNT (18537) | | C'-PRNT (18537) | |
|---|---|---|---|---|---|---|---|---|---|---|---|---|---|
| | | wk 3 | wk 6 | wk 3 | wk 6 | wk 3 | wk 6 | wk 3 | wk 6 | wk 3 | wk 6 | wk 3 | wk 6 |
| 1 μg IF | alum | nd[5] | 125.8 | <0.1 | <0.1 | <10 | 180 | <10 | 463 | <10 | 148 | 25 | 128 |
| | OS-21 | nd | 1000.2 | <0.1 | <0.1 | <10 | 156 | 18 | 842 | 13 | 2253 | 38 | 6652 |
| | 3D-MPL + alum | nd | 785.4 | <0.1 | <0.1 | <10 | 102 | <10 | 6344 | <10 | 389 | 29 | 6344 |
| .75 μg IF + | alum | nd | 306.3 | <0.1 | 2.6 | <10 | 49 | <10 | 139 | <10 | 282 | <10 | 343 |
| .25 μg IF + | OS-21 | nd | 637.1 | 4.5 | 141.8 | <10 | 847 | 12 | 6668 | 13 | 455 | 43 | 5300 |
| | 3D-MPL + alum | nd | 499.0 | ≦0.6 | 22.8 | <10 | 244 | <10 | 322 | <10 | 165 | 24 | 5704 |
| .5 μg IF | alum | 43.2 | 227.8 | <0.1 | 8.9 | <10 | 119 | 18 | 177 | <10 | 454 | 19 | 288 |
| .5 μg G | OS-2T | nd | 689.0 | 2.7 | 262.3 | <10 | 474 | <10 | 6992 | 18 | 383 | 78 | >10240 |
| | 3D-MPL | 19.3 | 87.3 | 18.3 | 88.7 | <10 | 71 | <10 | 3640 | 34 | 33 | 38 | 1586 |
| | 3D-MPL + alum | 55.8 | 291.01 | 6.1 | 69.5 | <10 | 36 | <10 | 8488 | 21 | 300 | 18 | 1899 |
| 1 μg PFP-1 | alum | 24.0 | 119.5 | <0.1 | 0.4 | <10 | 22 | <10 | 24 | <10 | 95 | 16 | 302 |
| | OS-21 | nd | 516.9 | <0.1 | 0.7 | <10 | 60 | <10 | 262 | <10 | 455 | <10 | 5704 |
| | 3D-MPL | 18.2 | 85.7 | <0.1 | ≦0.1 | <10 | 22 | <10 | 53 | <10 | 65 | 16 | 3592 |
| | 3D-MPL + alum | 39.0 | 169.6 | <0.1 | ≦0.6 | <10 | 70 | <10 | 111 | <10 | 270 | 22 | 1442 |
| 1 μg F/G chimeric | alum | 15.6 | 120.5 | 1.4 | 26.0 | <10 | 24 | <10 | 103 | <10 | 52 | <10 | 184 |
| | OS-21 | nd | 408.1 | 6.2 | 202.2 | <10 | 440 | 119 | 6388 | <10 | 777 | 557 | 7028 |
| | 3D-MPL | 18.5 | 81.0 | 13.9 | 77.3 | <10 | 29 | 46 | 2248 | <10 | 73 | 475 | 133 |
| | 3D-MPL + alum | 14.9 | 341.6 | 1.1 | 54.4 | <10 | 241 | 388 | 813 | <10 | 397 | 130 | 1711 |
| .75 μg IF | alum | 33.8 | 225.3 | <0.1 | <0.1 | <10 | 78 | <10 | 114 | <10 | 113 | <10 | 107 |
| | OS-21 | 38.7 | 593.4 | <0.1 | <0.1 | <10 | 53 | <10 | 502 | <10 | 141 | 20 | 5880 |
| | 3D-MPL + alum | 46.1 | 418.8 | <0.1 | <0.1 | <10 | 235 | <10 | 138 | <10 | 305 | 23 | 3880 |
| .5 μg IF | alum | 12.2 | 233.5 | <0.1 | <0.1 | <10 | 32 | <10 | 57 | <10 | 88 | <10 | 77 |
| | OS-21 | 14.6 | 120.0 | <0.1 | <0.1 | 10 | 35 | 16 | 433 | <10 | 70 | 19 | 546 |
| | 3D-MPL + alum | 21.9 | 254.8 | <0.1 | <0.1 | <10 | 73 | <10 | 278 | <10 | 947 | 29 | 3740 |

-continued

Immunogenicity of RSV F and G Proteins with Various Adjuvants[1]

| | | Serological Titers by Assay[2] and Time | | | | | | | | | | |
|---|---|---|---|---|---|---|---|---|---|---|---|---|
| | | EIA-F (×1000) | | EIA-Ga (×1000) | | PRNT (A2) | | C'-PRNT (A2) | | PRNT (18537) | | C'-PRNT (18537) | |
| Immunogen[3] | Adjuvant[4] | wk 3 | wk 6 | wk 3 | wk 6 | wk 3 | wk 6 | wk 3 | wk 6 | wk 3 | wk 6 | wk 3 | wk 6 |
| .5 µg G | alum | <0.1 | <0.1 | ≦0.4 | 43.6 | <10 | 14 | <10 | 20 | <10 | <10 | <10 | <10 |
| | OS-21 | <0.1 | <0.1 | <0.1 | 0.1 | <10 | <10 | <10 | <10 | <10 | <10 | <10 | <10 |
| | 3D-MPL | <0.1 | <0.1 | 7.0 | 85.2 | <10 | 14 | <10 | 5880 | 27 | <10 | 11 | 3376 |
| | 3D-MPL + alum | <0.1 | <0.1 | 45.6 | 204.6 | <10 | 55 | <10 | 2876 | 22 | <10 | <10 | <10 |
| .25 µg G | alum | <0.1 | <0.1 | ≦0.8 | 43.2 | <10 | <10 | <10 | 14 | <10 | <10 | <10 | <10 |
| | OS-21 | <0.1 | <0.1 | <0.1 | 0.7 | <10 | <10 | <10 | 17 | <10 | <10 | <10 | 41 |
| | 3D-MPL + alum | <0.1 | <0.1 | ≦0.2 | 0.9 | <10 | <10 | <10 | 272 | <10 | <10 | <10 | <10 |
| .05 µg G | alum | <0.1 | <0.1 | <0.1 | 2.3 | <10 | <10 | <10 | <10 | <10 | <10 | <10 | <10 |
| | OS-21 | <0.1 | <0.1 | <0.1 | 1.1 | <10 | <10 | <10 | 593 | <10 | <10 | <10 | 1300 |
| | 3D-MPL + alum | <0.1 | <0.1 | ≦0.7 | 5.5 | <10 | 14 | <10 | 181 | <10 | <10 | <10 | <10 |
| PBS | OS-21 | <0.1 | <0.1 | <0.1 | <0.1 | <10 | <10 | <10 | <10 | <10 | <10 | <10 | <10 |

[1] Seronegative Swiss Webster mice were immunized (100 µl) with F and G proteins in various adjuvants on week) and week 3. Mice were bled for serology on weeks 0, 3 and 6.
[2] Serological assays: EIA-F (F protein specific enzyme immunoassay), EIA-Ga (Ga protein specific enzyme immunoassay), PRNT (plaque reduction neutralization test) against a subgroup A strain of RSSV (i.e. A2) and a subgroup B strain of RSV (i.e. 18537). C'-PRNT (plaque reduction neutralization test with 5% complement) were also performed against RSV strains A2 and 18537. EIA assays were performed on individual sera and the geometric neon titers (GMT) were calculated and are re ported. PRNT and C'-PRNT assays were performed on pooled sera (one pool per group, n-5).
[3] Immunogens: IF- ion exchange purified RSV F protein; G-affinity purified RSV G protein; PFP-1- affinity purified RSV F protein; F/G chimeric-F/G chimeric protein purified from baculovirus-infected Sf9 culture.
[4] Immunogens were administered with the following adjuvants: Alum - 1 µg/ml aluminum hydroxide, OS-21 - 200 µg/ml OS-21, 3D-MPL-250 µg/ml 3D-MPL, 3D-MPL + alum- a combination of 250µ/ml 3D-MPL plus 1 µg/ml aluminum hydroxide.
[5] nd — not done.

Effect of Various Adjuvants on Immunogenicity of F and G in BALB/c Mice[1]

| | | Serological Titers by Assay[2] and Time | | | | | | | | |
|---|---|---|---|---|---|---|---|---|---|---|
| | | EIA-F (×1000) | | EIA-Ga (×1000) | | PRNT-RSV (A2) | | | PRNT-RSV (18537) | |
| Immunogen | Adjuvant | wk 4 | wk 8 | wk 4 | wk 8 | wk 4 | wk 8 | wk 8 + C' | wk 4 | wk 8 |
| IF | none | 0.3 | 9.0 | <0.1 | <0.1 | <10 | <10 | <10 | <10 | <10 |
| 0.5 µg | alum[3] | 10.1 | 96.9 | <0.1 | <0.1 | <10 | 11 | 33 | <10 | 41 |
| | OS21[4] | 59.9 | 874.5 | <0.1 | <0.1 | <10 | 213 | 108 | 59 | 152 |
| | 3D-MPL[5] | 2.7 | 85.6 | <0.1 | <0.1 | <10 | <10 | <10 | <10 | 21 |
| | alum + 3D-MPL[6] | 3.4 | 208.7 | <0.1 | <0.1 | <10 | 118 | 109 | <10 | 60 |
| IF + G | none | 0.4 | 26.8 | <0.1 | <0.1 | <10 | <10 | <10 | <10 | <10 |
| 0.5 µg | alum | 8.7 | 124.0 | <0.1 | 17.6 | <10 | 74 | 31 | 18 | 59 |
| | OS21 | 36.9 | 335.7 | 0.9 | 350.0 | <10 | 1604 | >10240 | 26 | 221 |
| CONTROLS: | 3D-MPL | 3.1 | 37.2 | 0.5 | 43.3 | <10 | 35 | 218 | <10 | 80 |
| RSV (IN) | none | 4.0 | 22.7 | 1.1 | 200.0 | 19 | 393 | 5760 | <10 | 53 |
| RSV (IM) | none | <0.1 | 21.8 | 0.3 | 17.2 | <10 | 71 | 960 | <10 | 41 |
| PBS | none | <0.1 | <0.1 | <0.1 | <0.1 | <10 | <10 | <10 | <10 | <10 |

[1] Seronegative Balb/C mice were immunized (100 µl) on weeks 0 and 4 with 0.5 µg doses of the various immunogens. Mice were bled for serology at weeks 0, 4 and 8.
[2] Serological assays: EIA-F (F protein specific enzyme immunoassay), EIA-GA (GA protein specific enzyme immunoassay), PRNT (Plaque reduction neutralization test) against a subgroup A strain of RSV (i.e. A2) and a subgroup B strain of RSV (i.e. 18537). All assays were performed on pooled sera (1 pool/group, n-5. Additionally, the week 8 pools were tested by Complement enhanced PRNT by the addition of 5% rabbit complement.
[3] Alum: Aluminum hydroxide, 1 mg/ml.
[4] 3D-MPL: 3D- Monophospholipid A, 250 µg/ml (25 µg/dose).
[5] OS21: 200 µg/µl (20 µg/dose).
[6] Alum + 3D-MPL: mixture of 1 mg/ml aluminum hydroxide and 250 µg/ml 3D-MPL.

TABLE 3

Dose Response of the Immunogenicity of IF with Various Adjuvants in Swiss Webster Mice[1]

| | | Serological Titers by Assay[2] and Time | | | | | | | | | |
|---|---|---|---|---|---|---|---|---|---|---|---|
| | | EIA-F (×1000) | | PRNT (A2) | | C'-PRNT (A2) | | PRNT (18537) | | C'-PRNT (18537) | |
| Immunogen[3] | Dose (µg) | wk 3 | wk 6 | wk 3 | wk 6 | wk 3 | wk 6 | wk 3 | wk 6 | wk 3 | wk 6 |
| IF/alum | 5 | ND[4] | 281.9 | <10 | 111 | 11 | 71 | <10 | 438 | 10 | 62 |
| | 0.5 | 18.6 | 232.6 | <10 | 62 | <10 | 23 | <10 | 181 | <10 | 164 |
| | 0.05 | 8.7 | ND | <10 | 39 | <10 | 30 | <10 | 227 | <10 | 82 |

TABLE 3-continued

Dose Response of the Immunogenicity of IF with Various Adjuvants in Swiss Webster Mice[1]

| | | Serological Titers by Assay[2] and Time | | | | | | | | |
|---|---|---|---|---|---|---|---|---|---|---|
| | | EIA-F (×1000) | | PRNT (A2) | | C'-PRNT (A2) | | PRNT (18537) | | C'-PRNT (18537) |
| Immunogen[3] | Dose (μg) | wk 3 | wk 6 | wk 3 | wk 6 | wk 3 | wk 6 | wk 3 | wk 6 | wk 3 | wk 6 |
| | 0.005 | 3.9 | ND | <10 | 21 | <10 | 21 | <10 | 50 | <10 | 166 |
| IF/OS-21 | 5 | ND | 1034.1 | <10 | 237 | 23 | 1057 | 16 | 2012 | 98 | 3988 |
| | 0.5 | ND | 831.9 | <10 | 151 | <10 | 2062 | <10 | <10 | 37 | 5768 |
| | 0.05 | <0.3 | ND | <10 | <10 | <10 | 23 | <10 | 18 | <10 | 74 |
| | 0.005 | <0.1 | ND | <10 | <10 | <10 | 11 | <10 | <10 | <10 | <10 |
| IF3D-MPL | 5 | 7.9 | 73.8 | <10 | 12 | <10 | 43 | <10 | 42 | <10 | 192 |
| | 0.5 | ND | ND | <10 | 28 | <10 | 136 | <10 | 343 | 19 | 1736 |
| | 0.05 | 4.9 | ND | <10 | 14 | <10 | 81 | <10 | 42 | 18 | 756 |
| | 0.005 | 1.3 | ND | <10 | <10 | <10 | 20 | <10 | <10 | <10 | 163 |
| IF/3D-MPL + | 5 | 28.6 | 386.7 | <10 | 87 | <10 | 134 | <10 | 660 | 26 | 448 |
| alum | 0.5 | ND | 301.7 | <10 | 373 | <10 | 128 | <10 | 372 | 28 | 937 |
| | 0.05 | 29.1 | ND | <10 | <10 | <10 | 116 | <10 | 161 | 21 | 1325 |
| | 0.005 | 3.2 | ND | <10 | <10 | <10 | 20 | <10 | <10 | <10 | 83 |
| PRS/OS-21 | — | <0.1 | ND | <10 | <10 | <10 | <10 | <10 | <10 | <10 | <10 |

[1]Seronegative Swiss Webster mice were immunized (100 μl) with ion exchange-purified RSV F protein (IF) or PBS in various adjuvants on week 0 and week 3. Mice were bled for serology on weeks 0, 3 and 6.
[2]Serological assays: EIA-F (F protein specific enzyme immunoassay), EIA-Ga (Ga protein specific enzyme immunoassay), PRNT (plaque reduction neutralization test) against a subgroup A strain of BSV (i.e. A2) and a subgroup B strain of RSV (i.e. 18537). C'-PRNT (plaque reduction neutralization test with 5% complement) were also performed against RSV strains A2 and 18537. EIA assays were performed on individual sera and the geometric mean titers (GMT) were calculated and are re ported. PRNT and C'PRNT assays were performed on pooled sera (one pool per group, n-5).
[3]Ion exchange-purified F protein (IF) was administered with the following adjuvants: alum = 1 mg/ml aluminum hydroxide, OS-21 = 200 μg/ml OS-21, 3D-MPL = 250 μg/ml 3D-MPL, 3D-MPL + alum = a mixture of 250 μg/ml 3D-MPL plus 1 mg/ml aluminum hydroxide.
[4]ND = Not done.

TABLE 4

Immunogenicity of RSV F and G Proteins with Aluminum Hydroxide or OS-21 in Swiss Webster Mice[1]

| | | Serological Titers by Assay[2] and Time | | | | | | | |
|---|---|---|---|---|---|---|---|---|---|
| | | EIA-F GMT (×1000) | | EIA-G GMT (×1000) | | PRNT-RSV (A2) | | PRNT-RSV (18537) | |
| Immunogen | Adjuvant | wk 3 | wk 6 | wk 3 | wk 6 | wk 3 | wk 6 | wk 3 | wk 6 |
| IF + G[3] | alum | 20.1 | 251.2 | ≦0.2 | 8.6 | <10 | 13 | 73 | 64 |
| 1 μg | OS-21 | 16.3 | 446.7 | 2.4 | 153.2 | <10 | 78 | 229 | 315 |
| IF[4] | alum | 28.1 | 275.4 | <0.1 | <0.1 | <10 | 25 | 26 | 139 |
| 1 μg | OS21 | 17.4 | 309.0 | <0.1 | <0.1 | <10 | <10 | <10 | <10 |
| PHS | OS21 | <0.1 | <0.1 | <0.1 | <0.1 | <10 | <10 | <10 | <10 |

[1]Seronegative mice were immunized (100 μL, IM) with 1 μg protein adjuvanted with either alum (AL (OB)$_3$, 1 mg/ml > or OS-21 (250 μg/ml) at weeks 0 and 3. Mice were bled for serology at weeks 0, 3, 6.
[2]Serological assays: EIA-F (F protein specific enzyme immunoassay), PRNT (plaque reduction neutralization test) for subgroup A strain of RSV (i.e. A2) and a subgroup B strain of RSV (i.e 18537) with the addition of 5% rabbit complement. EIA assays were performed on individual sera and the geometric mean titers (GMT) were calculated and are reported (#mice/group = 5).
[3]Ion-exchange purified F protein (triton X-100 lysis) combined with an equal quantity of affinity purified G protein (triton X-100/deoxycholate lysis).
[4]Ion-exchange purified F protein.

EXAMPLE 4

Virus and Cell Lines. The A2 and 18537 strains of RSV are used and virus stocks are grown in either Vero [American Type Culture Collection (ATCC) No. CCL 81] or HEp-2 (ATCC No. CCL 23) cells following standard procedures, purified over sorbitol density gradients and stored at −70° C. until use. A BCM4 cell line persistently infected with the Long strain of RSV and the uninfected BALB/c cell line (for both cell lines see Fernie et al., Proc. Soc. Exp. Biol. Med., 1981, 167: 83–86) are a gift of Dr. Bruce F. Fernie. The latter cell lines are maintained in Dulbecco's Modified Eagle's medium (DMEM, Gibco BRL, Gaithersburg, Md.) with 10% (V/V) heat-inactivated FBS (Hyclone Laboratories Inc., Logan, Utah).

EXAMPLE 5

Anti-F protein antibody subclass determination. The titer of anti-F protein antibody subclass of mice primed with 5 μg of F protein mixed with QS-21, ALOH or natural infection are determined by ELISA. Briefly, 96 well plates are prepared with the 20 ng F protein or 5 ug RSV A2 as follows. Purifed F protein (200 ng/ml) or RSV A2 (50 μg/ml) in carbonate/bicarbonate buffer (pH 9.6) is coated onto 96-well plates (Nunc, Roskilde, Denmark) for 2 h at 37° C. and stored overnight at 4° C. Thereafter, the plates are washed 5 times with PBS/0.05% Tween 20 (Sigma) followed by 2 additional rinses with PBS alone. Serial 3-fold dilutions of serum prepared in PBS/0.3% Tween 20/0.01M EDTA buffer (pH 7.0) are then added to the wells and incubated for 1 h at room temperature. After washing 5 times with PBS/0.1% Tween 20, 100 ul of biotinylated goat anti-mouse IgG (1:4000, Kirkegaard and Perry Laboratories), IgG1 (1:3000, Zymed), or IgG2a (1:5000, Zymed) is added and the plates are incubated 1 h at room temperature. Following another series of washes, 100 ul of strepavidin conjugated to horseradish peroxidase (1:10,000 dilution in PBS/0.3% Tween 20, Zymed) is added to the wells and incubated at room temperature for an additional 30 minutes. Peroxidase substrate (2,2'-azino-di[3-ethyl-benzthiazoline sulfonate (6)], Kirkegaard and Perry Laboratories) was added to the wells after washing and incubated at room temperature for 20 minutes at which time the reaction is stopped with 100 ul of 1% sodium dodecal sulphate (Pierce, Rockford, Ill.). End point titers are determined at 410 nM.

Virus Neutralization Assay (PRNT) is performed as in Example 3.

The heightened complement-assisted serum neutralizing antibody titers elicited by F/QS-21 correlated with the induction of anti-F protein antibodies of the IgG2a subclass (Table 5). Three weeks after primary immunization, there is a QS-21 dose-related increase in protein-specific IgG2a as well as IgG1 antibodies. In comparison, a single injection of F protein mixed in saline alone or F/ALOH elicits primarily protein-specific antibodies of the IgG1 subclass (Table 5). The data indicates that F/QS-21 induces humoral immune responses that are similar to those generated by experimental infection and consist of both complement-fixing IgG2a as well as IgG1 antibodies.

EXAMPLE 6

Determination of Cross Neutralizing Antibody Titers and RSV Infectivity. The titration of serum neutralizing antibody is performed in duplicate on HEp-2 cell monolayers in 96-well tissue culture plates as described in Example 3.

In this example, as shown in the table below, it is observed that an adjuvant can enable RSV protein to elicit a complement dependent IgG antibody response which neutralizes both subgroup A and subgroup B viruses (these subgroups being indentified as A2 and 18537, respectively in the table below). This cross neutralizing immune response of heterologous subtype RS virus has not been achieved before using purified G protein alone. A vaccine formulated with QS-21 adjuvant and RS virus G protein generates a desirable heterotypic neutralizing antibody response which is substantially greater than that which is elicted by alum alone or a natural infection.

TABLE 6

Heterotypic Neutralizing Antibody Response
Elicited by RSV G Protein When Adjuvanted with QS-21[1]

| Immunogen (µg)[3] | Adjuvant[4] | PRNT[2] | |
|---|---|---|---|
| | | A2 | 18537 |
| G protein (2.5) | QS-21 | 7940 | 6039 |
| G protein (1.2) | QS-21 | >10,240 | 5154 |
| G protein (0.6) | QS-21 | 2092 | 719 |
| G protein (0.3) | QS-21 | 308 | 1906 |

TABLE 6-continued

Heterotypic Neutralizing Antibody Response
Elicited by RSV G Protein When Adjuvanted with QS-21[1]

| Immunogen (µg)[3] | Adjuvant[4] | PRNT[2] | |
|---|---|---|---|
| | | A2 | 18537 |
| Controls: | | | |
| G protein (2.5) | alum | 212 | <10 |
| G protein (2.5) | none | <10 | <10 |
| PBS | QS-21 | <10 | <10 |

[1]Seronegative BALB/c mice are immunized (0.1 ml, I.M.) at weeks 0 and 3 with RSV G protein at the doses indicated above. Animals are challenged (0.1 ml, I.N.) with 6 $\log_{10}$ PFU of RSV strain A2 at week 6 and bled for serology at 4 days post-challenge.
[2]PRNT = plaque reduction neutralization test performed against a subgroup A (A2) and a subgroup B (18537) strain of RSV. Assays are performed on pooled sera (n = 5) in the presence of 5% rabbit complement.
[3]Immunogen: RSV G protein is immunoaffinity purified from Vero cell lysates infected with RSV strain A2. This purified protein is further processed using immunoaffinity chromatography to reduce the level of residual F protein. No detectable F protein-specific antibodies (as measured by EIA) are elicited by these immunogens.
[4]Adjuvants: QS-21 (200 µg/ml) or aluminum hydroxide (alum, 1 mg/ml) are mixed with RSV G protein or PBS 24 hours prior to use.

EXAMPLE 7

Comparison of QS-21 vs. ALOH for ability to elicit local F protein-dependent killer cell activity The ability of QS-21 to elicit local F protein-dependent killer cell activity is also examined and compared to the cell-mediated cytotoxicity generated by immunization with F/ALOH or experimental infection.

The Isolation of Pulmonary Mononuclear Cells (PMC). The PMC are isolated from the lungs following collagenase digestion (see Hancock et. al., Vaccine, 12: 267–274, 1994 and Anderson et. al., J. Gen. Virol., 71: 1561–1570, 1990). Briefly, excised lungs are placed in cold DMEM and rinsed free of peripheral blood. The lungs are then minced in fresh DMEM, transferred to a 50 ml centrifuge tube and nutated at 37° C. in the presence of collagenase (collagenase type IV, Sigma Chemical Co., St. Louis, Mo.) at a final concentration of 2 mg/ml, 10 mM HEPES buffer, and 1% (V/V) heat-inactivated FBS. After 90 minutes incubation, the fragments are passed through a 100 mesh stainless steel tissue culture seive (Sigma). The resulting suspension is pelleted (400 g), resuspendend in metrizamide (16%, W/V, Accurate Chemical & Scientific Corp., Westbury, N.Y.), overlayed with RPMI 1640 (Gibco BRL) containing 10% heat-inactivated FBS, and spun (150 g) for 20 minutes at 5° C. The PMC layers are then collected, washed free of gradient, and tested ex vivo for their cytolytic capacity.

Determination of Percent Cytotoxicity. Antigen-dependent cellular cytotoxicity is determined in a 4 h $^{51}$Cr (Amersham Corp., Arlington Heights, Ill.) release assay. Briefly, 50 ul (5000 cells) of syngeneics$^{51}$Cr-labeled control or RSV-infected (BCH4) target cell lines are incubated (37° C., 5% $CO_2$) in triplicate V-bottom micro-wells (Costar, Cambridge, Mass.) with 100 ul of spleen or pulmonary mononuclear cells (serially 2-fold diluted in RPMI 1640 containing 10% heat-inactivated FBS, V/V). The final volume is 150 ul per well. After incubation, the supernatants are collected (Skatron Harvester, Skatron Inc., Sterling, Va.), measured for $^{51}$Cr release in a ClinGamma counter (Pharmacia LKB), and compared with spontanteous release (targets incubated with medium alone, 20–25%) and total release (targets incubated in culture medium with 1.0% Triton X-100, V/V in PBS). Percent specific release is calculated by: 100 X [(mean cpm experimental)—(mean cpm spontaneous release)]/[(mean cpm total release)—(mean cpm spontaneous release)].

Antibody Blocking Studies. Purified monoclonal antibodies directed against major histocompatibility complex (MHC) antigens H2K$^d$ (clone SFi-1.1, IgG 2a), H-2D$^d$ (clone AF4-62.4, IgG 2b), and H-2K$^b$ (clone AF6-88.5, IgG 2a) are purchased from PharMingen, San Diego, Calif. A monoclonal antibody (E37-10, IgG 2b) directed against diphtheria toxoid antigen serves as subclass control. The monoclonal antibody directed against murine CD8 surface molecules (53–6.72, ATCC No. TIB 105) is purified from hybridoma culture supernatants over a recombinant protein G column (Pharmacia). Purified rat IgG is purchased from Calbiochem (San Diego, Calif.). To block cell-mediated cytolysis, 50 ul antibody is added to 50 ul effector cells prior to the addition of 50 µl of target cells. The final effector to target ratio was 60:1.

Figure 1A:
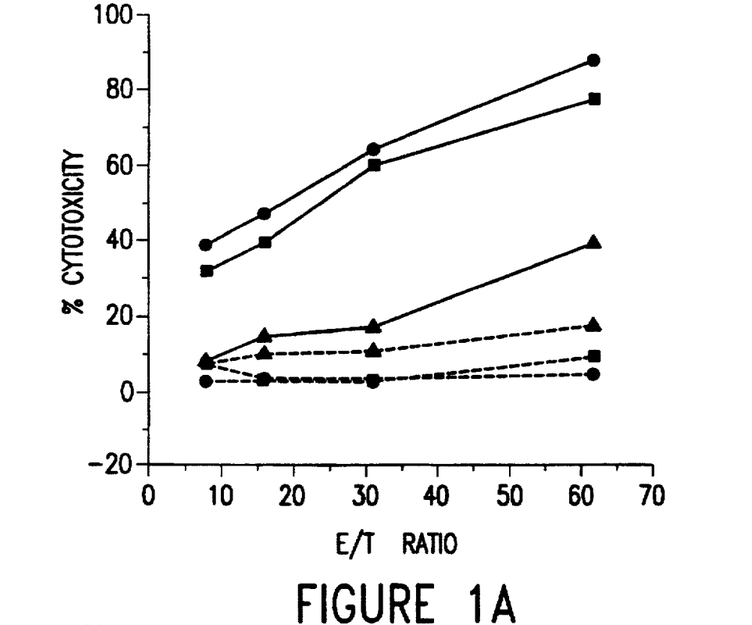
FIGS. 1A, 1B and 1C depict the cell-mediated cytoxicity results from the experiments of Example 5, which is discussed herein.

Balb/c mice are vaccinated at weeks 0 and 3 with 5 µg of F protein mixed with either 20 µg QS-21 ( ) or 100 µg ALOH (Δ) and compared to mice immunized by experimental infection (●). Two weeks after secondary immunization, the mice are challenged with virus. Four days after challenge, the PMC from BALB/c mice vaccinated with F/QS-21 are able to kill RSV-infected targets (solid lines in Figure) in an antigen-dependent manner (see FIG. 1A). Most noteworthy, this cytotoxic activity is as potent as that of the PMC from mice previously infected with RSV and nearly 3-fold greater than the activity induced in the PMC of mice vaccinated with F/ALOH. Control syngeneic targets (dashed lines) not infected with RSV are not killed (FIG. 1A). The activity is local because the spleen cells from the same mice are not cytolytic.

Figure 1B:
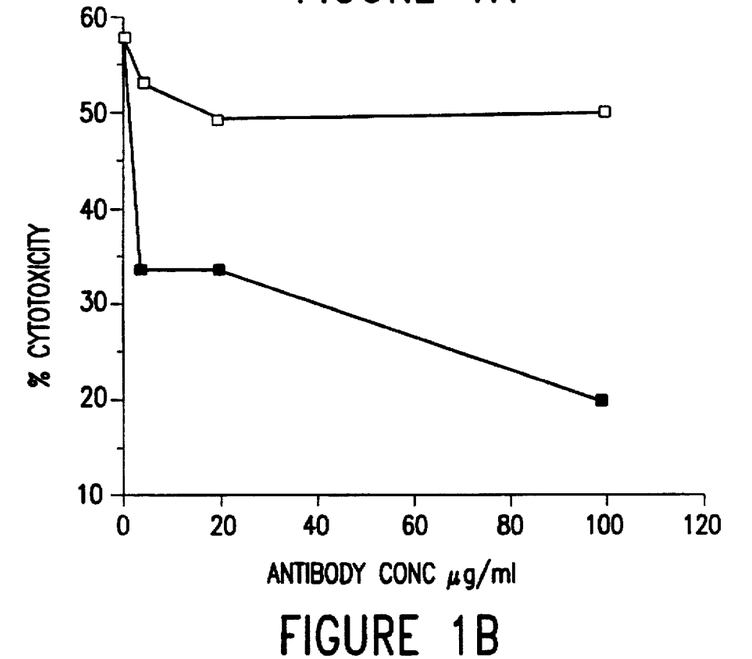
Figure 1C:
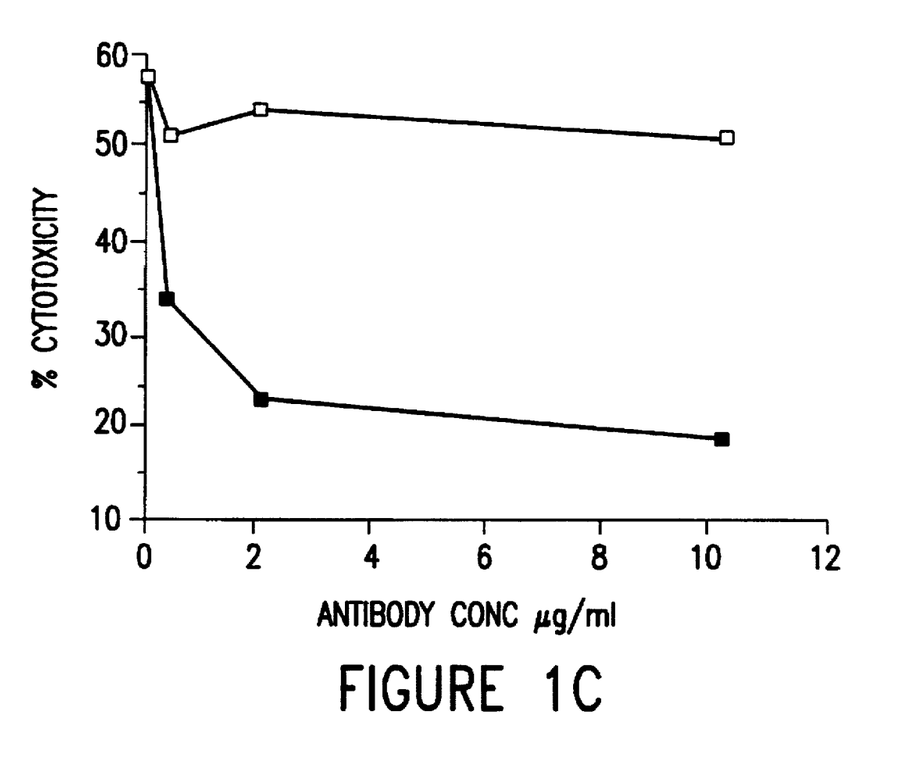

The results further suggested that the local killer cell activity induced by the F/QS-21 vaccine is mediated by T cells of the CD8 phenotype. Cytolysis was inhibited when increasing doses of monoclonal antibody directed against cells bearing CD8 surface determinants (filled symbol) are added to the assay mixture (FIG. 1B). Likewise, increasing concentrations of anti-H2D$^d$ and H2K$^d$ monoclonal antibodies (filled symbol) block cytolysis (FIG. 1C). Control immunoglobulin (open symbols) is not inhibitory (FIG. 1 B&C).

We claim:

1. A vaccine formulation comprising (a) a respiratory syncytial viral (RSV) protein selected from the group consisting of (i) RSV glycoprotein G, (ii) RSV glycoprotein F, (iii) a chimeric glycoprotein consisting of the signal and extracellular domains of RSV glycoprotein F linked to the extracellular domain of RSV glycoprotein G, and (iv) combinations thereof, and (b) an adjuvant selected from the group consisting of QS-21, 3-deacylated monophosphoryl lipid A and combinations thereof, in a physiologically acceptable vehicle.

2. A vaccine formulation comprising (a) a respiratory syncytial viral (RSV) protein selected from the group consisting of (i) RSV glycoprotein G, (ii) RSV glycoprotein F, (iii) a chimeric glycoprotein consisting of the signal and extracellular domains of RSV glycoprotein F linked to the extracellular domain of RSV glycoprotein G, and (iv) combinations thereof, and (b) QS-21, in a physiologically acceptable vehicle.

3. The vaccine formulation of claim 1 further comprising alum.

4. The vaccine formulation of claim 2 further comprising alum.

5. A vaccine formulation comprising (a) a respiratory syncytial vital (RSV) protein selected from the group consisting of (i) RSV glycoprotein G, (ii) RSV glycoprotein F, (iii) a chimeric glycoprotein consisting of the signal and extracellular domains of RSV glycoprotein F linked to the extracellular domain of RSV glycoprotein G, and (iv) combinations thereof, and (b) alum and 3-deacylated monophosphoryl lipid A, in a physiologically acceptable vehicle.

6. A method of protecting against lower respiratory disease and other disease symptoms of RSV infection in an individual comprising administering an effective amount of the vaccine of any one of claims 1, 2, 3, 4 or 5.

* * * * *